(12) United States Patent
Sournac et al.

(10) Patent No.: US 9,642,718 B2
(45) Date of Patent: May 9, 2017

(54) INTERVERTEBRAL DISC PROSTHESIS

(71) Applicant: MEDICREA INTERNATIONAL, Neyron (FR)

(72) Inventors: Denys Sournac, Reyrieux (FR); Thomas Mosnier, Anthon (FR); David Ryan, Collonges au Mont d'Or (FR)

(73) Assignee: Medicrea International, Neyron (FR)

( * ) Notice: Subject to any disclaimer, the term of this patent is extended or adjusted under 35 U.S.C. 154(b) by 293 days.

(21) Appl. No.: 14/350,244

(22) PCT Filed: Oct. 17, 2012

(86) PCT No.: PCT/IB2012/055637
§ 371 (c)(1),
(2) Date: Apr. 7, 2014

(87) PCT Pub. No.: WO2013/057663
PCT Pub. Date: Apr. 25, 2013

(65) Prior Publication Data
US 2014/0350681 A1 Nov. 27, 2014

(30) Foreign Application Priority Data
Oct. 19, 2011 (FR) ...................... 11 59452

(51) Int. Cl.
*A61F 2/44* (2006.01)
*A61F 2/30* (2006.01)

(52) U.S. Cl.
CPC ...... *A61F 2/4425* (2013.01); *A61F 2002/302* (2013.01); *A61F 2002/305* (2013.01);
(Continued)

(58) Field of Classification Search
CPC ........ A61F 2/4425; A61F 2/441; A61F 2/446; A61F 2/4465; A61F 2/447; A61F 2/442;
(Continued)

(56) References Cited

U.S. PATENT DOCUMENTS 3,219,305 A * 11/1965 Chartet ................... F16F 1/373
267/140.3
7,708,777 B2 * 5/2010 O'Neil .................. A61F 2/4425
623/17.13
(Continued)

FOREIGN PATENT DOCUMENTS

| WO | WO2008/094260 | 8/2008 |
| WO | WO2009074915 | 6/2009 |
| WO | WO2009/118691 | 10/2009 |

*Primary Examiner* — Tatiana Nobrega
*Assistant Examiner* — Marcela I Shirsat
(74) *Attorney, Agent, or Firm* — Defillo & Associates, Inc.; Evelyn A Defillo

(57) ABSTRACT

This prosthesis (1) includes two plates and an intermediate damping core (4) placed between both of these plates, this core (4) comprising a first shell (6) and a flexible element placed between this first shell (6) and a part for receiving the core. The first shell (6) and the first receiving part include means (18, 26) for guiding their mutual movement for bringing them closer or moving them away from each other. According to the invention, the receiving part includes a cavity intended to snugly receive the flexible element. The cavity being delimited by a first peripheral wall and by a bottom wall. The first peripheral wall having an external peripheral face; and the first shell (6) has a second peripheral wall forming an internal face. The internal face, when the first shell (6) and the receiving part are in their assembling condition, coming into close proximity to said external peripheral face and being able to slide along the latter.

10 Claims, 4 Drawing Sheets

(52) U.S. Cl.
CPC ............... *A61F 2002/30069* (2013.01); *A61F 2002/30224* (2013.01); *A61F 2002/30331* (2013.01); *A61F 2002/30365* (2013.01); *A61F 2002/30369* (2013.01); *A61F 2002/30372* (2013.01); *A61F 2002/30373* (2013.01); *A61F 2002/30563* (2013.01); *A61F 2002/30601* (2013.01); *A61F 2002/30604* (2013.01); *A61F 2002/30616* (2013.01); *A61F 2002/30649* (2013.01); *A61F 2002/30841* (2013.01); *A61F 2002/443* (2013.01)

(58) Field of Classification Search
CPC ...... A61F 2002/30069; A61F 2002/302; A61F 2002/30224; A61F 2002/30331; A61F 2002/30365; A61F 2002/30369; A61F 2002/30372; A61F 2002/30373; A61F 2002/305; A61F 2002/30563; A61F 2002/30601; A61F 2002/30604; A61F 2002/30616; A61F 2002/30649; A61F 2002/30841; A61F 2002/443; A61F 2002/30565; A61F 2002/30378; A61F 2002/30329; A61F 2002/30657; A61F 2002/3066; A61F 2002/30621
USPC ........................................ 269/159, 158, 153
See application file for complete search history.

(56) References Cited

U.S. PATENT DOCUMENTS

| | | |
|---|---|---|
| 2004/0024460 A1 | 2/2004 | Ferree |
| 2004/0054411 A1 | 3/2004 | Kelly |
| 2004/0243238 A1* | 12/2004 | Arnin ................ A61F 2/4425 623/17.12 |
| 2005/0038515 A1 | 2/2005 | Kunzler |
| 2005/0165485 A1* | 7/2005 | Trieu ................ A61F 2/4425 623/17.13 |
| 2006/0190084 A1 | 8/2006 | Doubler |
| 2009/0043391 A1* | 2/2009 | de Villiers ............ A61F 2/4425 623/17.16 |
| 2009/0192617 A1 | 7/2009 | Arramon |

* cited by examiner ered to the respective vertebrae and an intermediate damping core placed between both of these plates, is known. The prosthesis may be of the type with a dual articular movement, i.e. having both of its plates jointed relatively to the intermediate core; in this case, the intermediate core comprises two shells forming two articular surfaces for cooperating with conjugate articular surfaces possessed by the plates, and a flexible element placed between both of these shells. The prosthesis may also be of the type with a simple articular movement, i.e. having a single one of these two plates jointed relatively to the intermediate core; in this case, the intermediate core is formed by a shell or by a flexible element placed between this shell and the non-jointed plate, the flexible element fixedly received by this non-jointed plate.

The existing intervertebral disc prostheses of either one of these two types, do not give perfect satisfaction. Notably, they do not always perfectly reproduce the damping characteristics exhibited by natural vertebral discs. Further, the repeated movements which they undergo, result in more or less rapid wear of the flexible damping elements, which wear leads to an alteration of the articular movement.

When the intermediate core is mobile relatively to both plates, there moreover exists a notable risk of this core being expelled.

Further, the existing prostheses may be relatively complex to assemble.

The publication of patent application No. US 2009/192617 A1 describes an intervertebral disc prosthesis including two plates intended to be anchored to the respective vertebrae, and an intermediate damping core placed between both of these plates, this intermediate core comprising a first shell forming an articular surface for cooperating with a conjugate articular surface possessed by a first plate, and a flexible element placed between this first shell and a part for receiving this core, said first shell and said first receiving part comprising means for guiding their mutual movement for bringing them closer or moving them away from each other, made possible by the flexibility of said flexible element.

OBJECTS OF THE INVENTION

The present invention aims at finding a remedy to the whole of the aforementioned drawbacks.

Its main object is therefore to provide an intervertebral disc prosthesis allowing perfect reproduction of the damping movements which natural vertebral discs have.

Another object of the invention is to provide a prosthesis in which the wear of the flexible element is reduced.

Still another object of the invention is to provide a prosthesis with a dual articular movement, in which the intermediate core has a low risk of being expelled.

An additional object of the invention is to provide a prosthesis which is relatively simple to assemble.

SUMMARY OF THE INVENTION

The relevant prosthesis is of the aforementioned type. According to the invention, said receiving part comprises a cavity intended to snugly receive the flexible element, this cavity being delimited by a first peripheral wall and by a bottom wall, said first peripheral wall having an external peripheral face; and said first shell has a second peripheral wall forming an internal face, this internal face, when said first shell and the receiving part are in their assembling condition, coming into close proximity to said external peripheral face and being able to slide along the latter.

The guiding means which the prosthesis comprises, give the possibility of suppressing the risk of forces being exerted transversely to this movement on the flexible element, with the risk of causing shearing of this flexible element.

According to an embodiment of the invention, said cavity which said receiving part comprises, has an undercut shape, i.e. it has an opening for introducing the flexible element with a smaller section than the section which this cavity has underneath this opening, said flexible element being deformable so as to be able to forcibly cross the edge of said first peripheral wall delimiting this opening;

said flexible element comprises a third peripheral wall intended to be placed along the internal face of said first peripheral wall of the receiving part, a first end face connected to this third peripheral wall and a housing opening into its second end face, opposite to said first end face; said housing comprises an undercut shape, i.e. it has an opening with a smaller section than the section which this housing has underneath this opening; and said first shell has a stud suitable for being snugly placed in this housing, this stud having, at its free end, a larger section than the one which it has at its base, and said flexible element being deformable so that this stud may forcibly cross the edge of said third peripheral wall of the flexible element delimiting said opening.

The intermediate core is thus easy to assemble, by forcibly inserting the flexible element into said cavity and forcibly inserting said stud into said housing. The flexible element, thus structured as a cup and closely contained in a cavity, moreover allows the prosthesis to perfectly reproduce the damping movements which natural vertebral discs have.

According to another aspect of the invention, said first peripheral wall and the bottom wall delimiting said cavity are connected to each other through a first rounded wall having a first radius of curvature;

said third peripheral wall and said first end face of the flexible element are connected to each other through a second rounded wall having a second radius of curvature, this second radius of curvature being larger than the first radius of curvature so that, when said flexible element is engaged into said cavity, there exists a peripheral space between said second rounded wall of the flexible element and said first rounded wall of said receiving part; said first end face of the flexible element has a central recess giving it a concave shape, this recess being such that there exists, when said flexible element is engaged into said cavity, a central space between this first end face and said bottom wall.

Thus, said peripheral space and said central space are laid out between the flexible element and said receiving part; the flexible element, when it is subject to a pressure along a direction perpendicular to said bottom wall, deforms at its first end face, which causes the rounded wall of the flexible element to move towards the rounded wall of the receiving part, until it comes into contact with this wall.

Non-linear damping is thereby obtained, the degree of which is strongly reduced when this contact has occurred. This non-linear damping when a plate is brought closer to the other, corresponds to the damping produced by native vertebral discs, and is obtained with low wear of the flexible element.

According to a possibility, the surface of said bottom wall delimiting the bottom of the cavity is planar, and said central recess is such that said first end face of the flexible element comes into contact with this planar surface when the rounded wall of the flexible element comes into contact with said first rounded wall of the receiving part.

Thus, if the movement of the plates towards each other is continued, a reduction in the degree of the damping allowed by the prosthesis occurs, depending on the compressibility degree of the material making up the flexible element. When this compressibility degree is small, said reduction in the damping degree is therefore strong.

According to another possibility, the surface of said bottom wall delimiting the bottom of the cavity has a concave recess allowing additional flexural deformation of the flexible element beyond the point when said second rounded wall of the flexible element comes into contact with said first rounded wall of the receiving part.

Continuation of this deformation is thus possible beyond this contacting.

When the prosthesis is of the aforementioned type with a dual articular movement, i.e. when both plates are jointed relatively to the intermediate core, said receiving part is formed by a second shell forming an articular surface cooperating with a conjugate articular surface possessed by the second plate.

When the prosthesis is of the type with a single articular movement, i.e. when only one of the two plates is jointed relatively to the intermediate core, this receiving part is formed by the second plate itself.

The articular surface formed by said first shell and said conjugate articular surface possessed by said first plate are preferably portions of a sphere.

The articular surface formed by said second shell and said conjugate articular surface possessed by the second plate of the prosthesis are preferably portions of a sphere.

Advantageously, said second radius of curvature is 30 to 50% larger than said first radius of curvature, and is preferably larger by about 40% than this first radius of curvature.

Preferably, when the prosthesis is of the aforementioned type with a dual articular movement, said conjugate articular surface of the second plate is formed by the bottom of a recess delimited by a protruding circular wall, this protruding circular wall having an internal face tilted towards the inside of this recess;

the lower shell comprises a base with smaller dimensions than those of the recess delimited by said protruding circular wall, the edge of which has a tilt corresponding to that of the internal face of this wall.

This wall thereby provides some retention of said base in said recess.

BRIEF DESCRIPTION OF THE DRAWINGS

The invention will be well understood, and other features and advantages thereof will become apparent, with reference to the appended schematic drawing, illustrating three possible embodiments of the relevant prosthesis as non-limiting examples.

DESCRIPTION OF THE PREFERRED EMBODIMENTS

Figure 1:
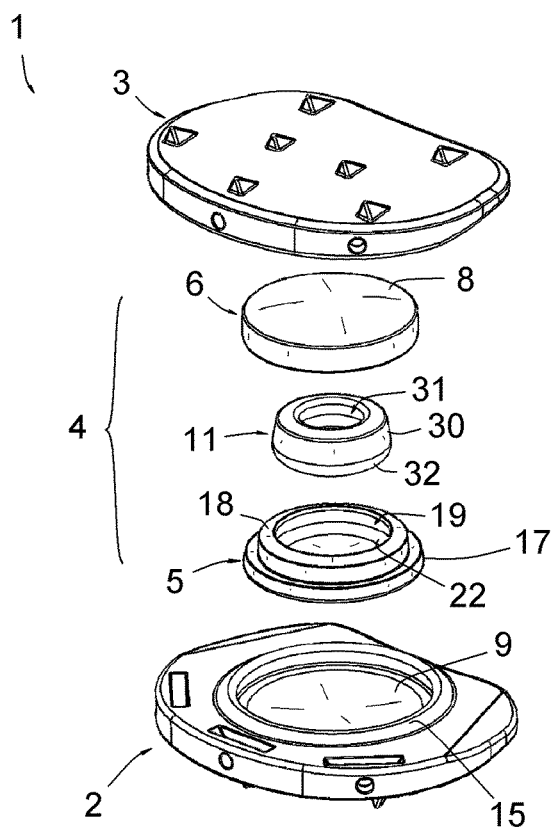
FIG. 1 is a perspective view thereof, before assembling, according to a first embodiment.
Figure 2:
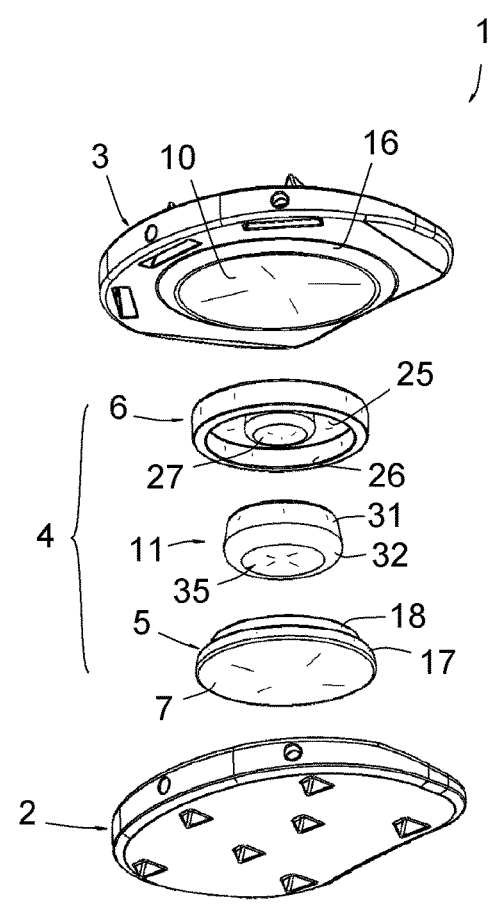
FIG. 2 is a view thereof similar to FIG. 1, according to another viewing angle.
Figure 3:
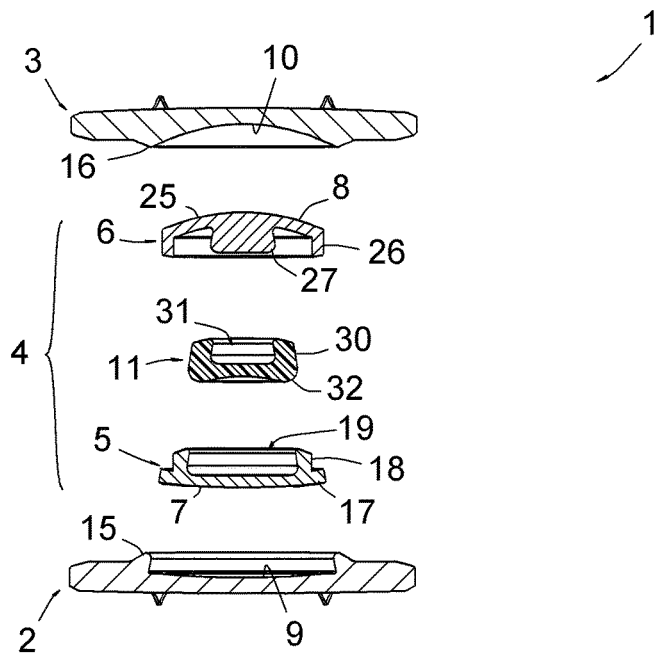
FIG. 3 is a transverse sectional view thereof, before assembling.

For the sake of simplification, the portions or elements of the first embodiment, which are found in an identical or similar way in the second embodiment, will be designated by the same numerical references.

FIGS. 1 to 5 illustrate an intervertebral disc prosthesis 1 comprising two vertebral plates 2, 3 intended to be anchored to respective vertebrae to be fitted with a prosthesis, and an intermediate damping core 4, placed between both of these plates. The prosthesis 1 is, in these figures, of the type with a dual articular movement, i.e. with its two plates 2, 3 jointed relatively to the intermediate core 4; in this case, the intermediate core comprises two shells 5, 6 forming two articular surfaces 7, 8 for cooperating with conjugate articular surfaces 9, 10 possessed by the plates 2, 3, and a flexible element 11 placed between both of these shells 5, 6.

The lower plate 2 has a lower face for bearing against the vertebral plate of the underlying vertebra, from which protrude insertion studs in the wall of this vertebral plate. On its upper face, the plate 2 has a circular central recess delimited by a protruding circular wall 15 and a bottom wall. As shown by the figures, and more particularly FIGS. 4 and 5, the wall 15 has an internal face tilted towards the inside of the recess, and the bottom wall forms a spherical and concave internal face, forming one of said conjugate articular surfaces 9.

The upper plate 3 has an upper face for bearing against the vertebral plate of the underlying vertebra, from which protrude insertion studs in the wall of this vertebral plate. On its lower face, the plate 3 has a circular central boss 16, the spherical and concave bottom of which forms the second of said conjugate articular surfaces 10.

The lower shell 5 comprises a circular base 17 with a slightly spherical shape and a circular wall 18 delimiting a central cavity 19 intended to snugly receive the flexible element 11.

The base 17 forms a spherical and convex lower face forming a first of said articular surfaces 7, capable of cooperating congruently with the conjugate articular surface 9 in order to allow the jointing of the lower plate 2 relatively to the intermediate core 4. As shown more particularly by FIGS. 4 and 5, the diameter of this base 17 is smaller than the diameter of the recess delimited by the wall 15, in order to allow this jointing. By means of its tilted internal face, the wall 15 provides some retention of the base 17 in the recess delimited by this wall 15; the edge of the base 17 also has a tilt corresponding to that of the internal face of this wall, for letting this edge come into contact with said internal face with a significant contact surface area.

The circular wall 18 forms a radially internal face delimiting the periphery of the cavity 19 and a radially external face. As this is visible in FIG. 6, this radially internal face is tilted towards the inside of the cavity 19, i.e. it has a frusto-conical shape having a larger section at its lower end and a smaller section at the upper opening of the cavity 19. The latter therefore has an undercut shape, i.e. its upper opening, for introducing the flexible element 11 into it, has a smaller section than the section which it has underneath this opening, said flexible element 11 being deformable so as to be able to forcibly cross the upper edge of the wall 18.

Figure 4:
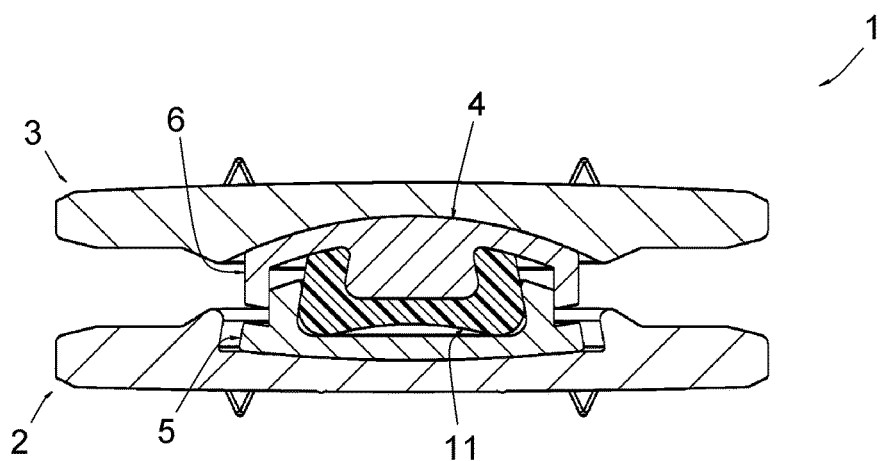
FIG. 4 is a transverse sectional view thereof, after assembling, at an enlarged scale, in a condition of non-compression of an intermediate core which the prosthesis comprises.
Figure 5:
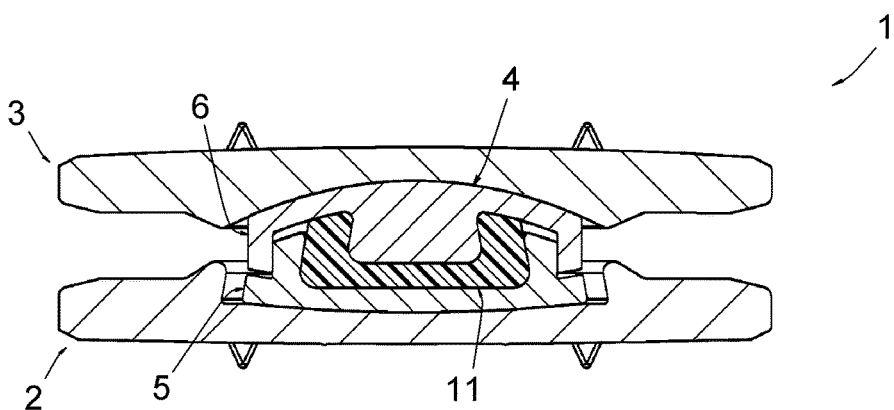
FIG. 5 is a view thereof, similar to FIG. 4 in a condition of compression of this intermediate core.
Figure 6:
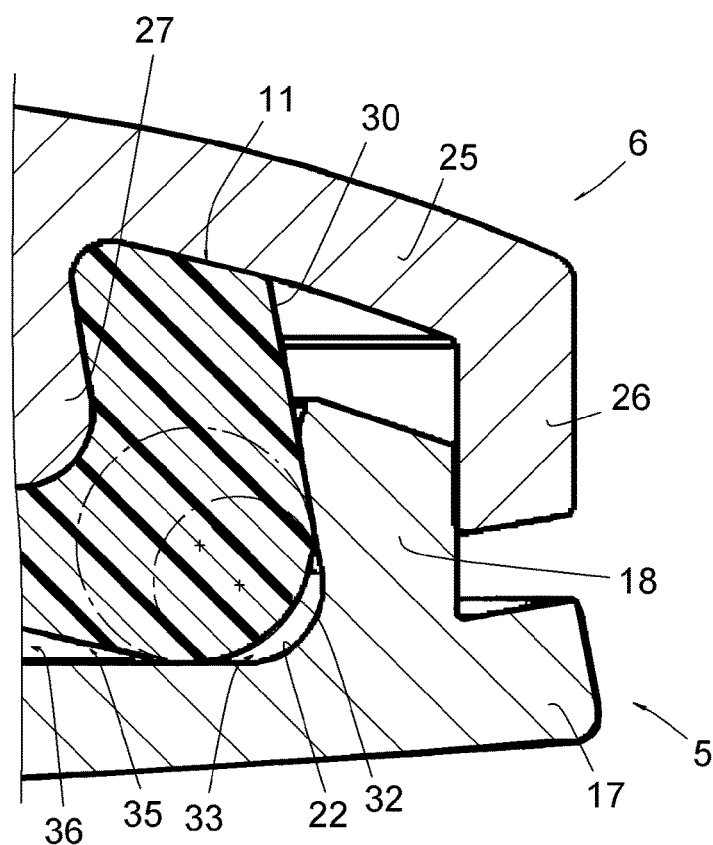
FIG. 6 is a partial view of the intermediate core, at a highly enlarged scale, with illustration of two circles coinciding with the curvatures of two rounded walls which this core comprises.

The upper edge of the wall 18 is chamfered so as to have a tilt corresponding to the tilt possessed by the wall of the facing shell 6, as shown by FIGS. 4 to 6.

The cavity 19 is also delimited by a bottom wall, the internal face of which is planar and is connected to the radially internal face of the wall 18 through a rounded wall 22 having a first radius of curvature (c.f. FIG. 6).

The upper shell 6 comprises a wall 25 with a spherical shape, a peripheral wall 26 and a central stud 27.

The wall 25 forms a convex spherical upper face, forming the second of the articular surfaces 8, which is capable of cooperating, congruently, with the conjugate articular surface 10 of the plate 3 in order to allow the jointing of the upper plate 3 relatively to the intermediate core 4.

The peripheral wall 26 forms a radially internal face, when both shells 5, 6 are in their assembling state as shown in FIGS. 4 to 6, coming into close proximity to the external peripheral face of the wall 18 and being able to slide along the latter.

The stud 27 has a frusto-conical shape, having at its free end, a larger section than the one it has at its base connected to the wall 25.

The flexible element 11 has a cup shape, with a peripheral wall 30 and a bottom wall delimiting a central housing 31 intended to snugly receive the stud 27.

The peripheral wall 30 has a frusto-conical shape, with a larger section on the side of the bottom wall and a smaller section on the side of its free edge. It forms an external peripheral face intended to be placed along the internal face of the wall 18, by snugly fitting the latter, and an internal peripheral face tilted towards the inside of the housing 31.

This external peripheral face is connected to a lower end face of the element 11 through a round wall 32 having a second radius of curvature, this second radius of curvature being 40% larger than the aforementioned first radius of curvature (c.f. FIG. 6, in which are illustrated the circles coinciding with the profile of the rounded walls 22 and 32, as well as crosses appearing in the centers of these circles). Thus, when the flexible element 11 is engaged into the cavity 19, there exists a peripheral space 33 between the rounded wall 32 and the rounded wall 22.

The upper edge of the wall 30 is also chamfered so as to have a tilt adapted to the shape of the internal face of the wall 25.

Said lower end face of the flexible element 11 has a central recess 35 giving it a concave shape, this recess 35 being such that when the flexible element 11 is engaged into the cavity 19, there is a central space 36 between this first end space and the internal face of the base 17 of the shell 5.

The housing 31 also has, because of the tilt of the radially internal face of the wall 30, an undercut shape, i.e. it has an opening for introducing the stud 27, having a smaller section than the section which this housing 31 has underneath this opening. The flexible element 11 is also deformable so that this stud 27 may forcibly cross the upper edge of the wall 30.

As this may be understood by comparing FIGS. 4 and 5, the flexible element 11, when it is subject to pressure transmitted by the plates 2, 3 tending to bring the shells 5, 6 closer, deforms at the first end face, which leads to gradual filling of said central space 36 and presses the rounded wall 32 of the flexible element 11 against the rounded wall 22 of the shell 5; this pressure produces a deformation of the flexible element 11 over the whole of its periphery and leads to the filling of said peripheral space 33; if the pressure experienced by the flexible element 11 continues, a reduction in the damping degree allowed by the prosthesis 1, occurs depending on the compressibility degree of the material making up the flexible element 11. When this compressibility degree is low, said reduction in the damping degree is therefore strong.

Figure 7:
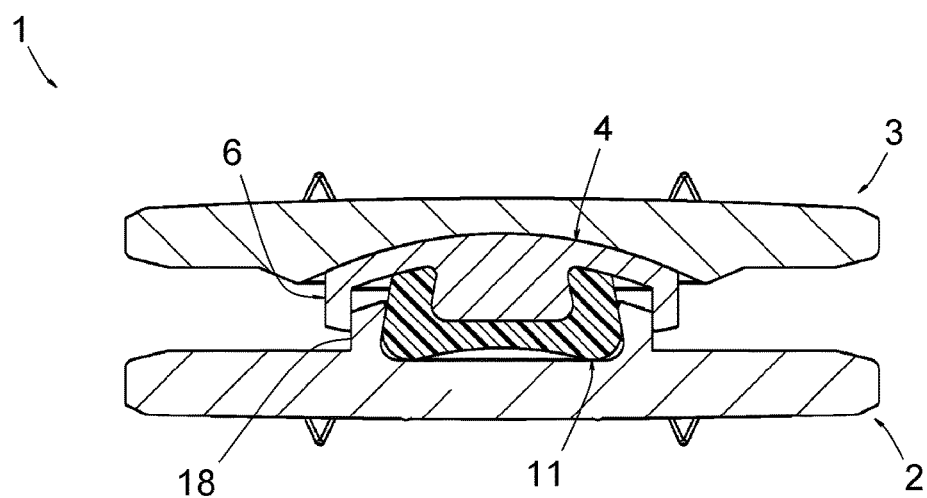
FIG. 7 is a view of the prosthesis according to the second embodiment.

FIG. 7 illustrates another embodiment of the prosthesis according to the invention, very similar to the one described earlier, except that this prosthesis 1 is of the type with a single articular movement, i.e. with a single one of both of its plates jointed relatively to the intermediate core 4 (this is the upper plate 3 in the illustrated example). The wall 18 then forms a body with the lower plate 2 and the intermediate damping core 4 is only formed with the upper shell 6 and the flexible element 11.

Figure 8:
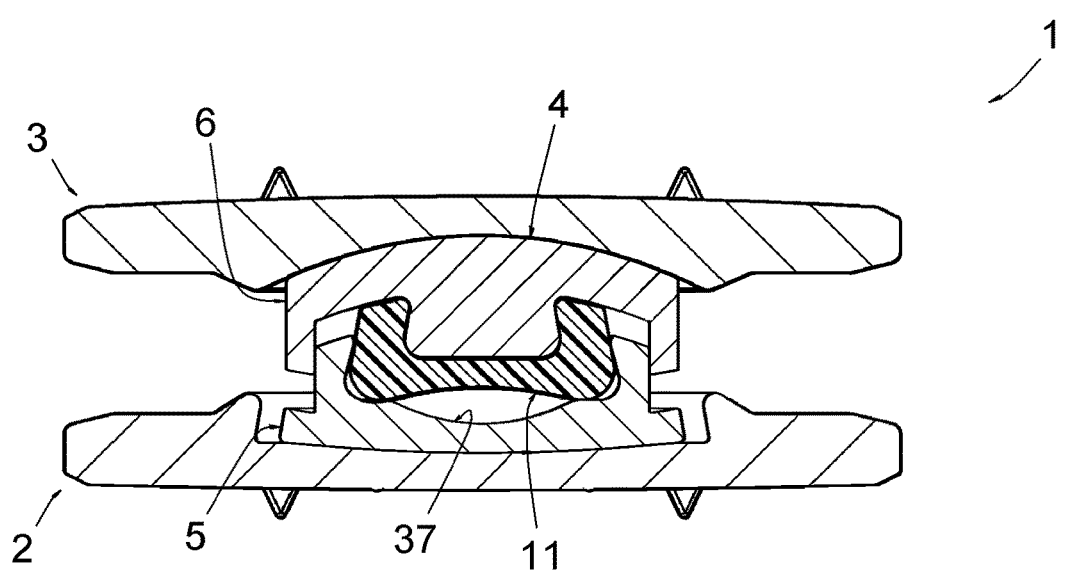
FIG. 8 is a view of the prosthesis similar to FIG. 4 according to a first embodiment.

FIG. 8 shows a prosthesis 1 similar to the one shown by FIGS. 1 to 6, except that the face delimiting the bottom of the cavity 19 is not planar but has a concave central recess 37 allowing additional flexural deformation of the flexible element 11 beyond the point when the rounded wall 32 of the flexible element 11 comes into contact with the rounded wall 22 of the lower plate 2.

Continuation of this deformation is thus possible beyond this contacting.

As this appears from the foregoing, the invention provides an intervertebral disc prosthesis, having determining advantages as compared with the homologous prosthesis of the prior art, in particular:

providing a prosthesis which is relatively simple to assemble and allowing perfect reproduction of the damping movements which natural vertebral discs have, by the aforementioned dual damping phase;

providing a prosthesis in which the wear of the flexible element 11 is reduced;

providing a prosthesis with a dual articular movement, in which the intermediate core 4 has a low risk of being expelled.

The invention has been described above with reference to embodiments given as examples. It is obvious that it is not limited to these embodiments but that it extends to all the other embodiments covered by the appended claims.

What is claimed is:

1. An intervertebral disc prosthesis comprising:
   a first plate and a second plate, the first plate anchored to a first vertebrae and the second plate anchored to a second vertebrae; and
   an intermediate damping core placed between the first plate and the second plate, the intermediate core comprising:

a first shell forming a first articular surface for cooperating with a conjugate articular surface possessed by the first plate, the first shell including a base, a first peripheral wall delimiting a central cavity;

a second shell forming a second articular surface for cooperating with a conjugate articular surface possessed by the second plate, the second shell including a second peripheral wall having a circular shape and a central stud; and a flexible element placed between the first shell and the second shell, the flexible element having the shape of a cup with an internal housing, the flexible element is tightly secured inside the central cavity of the first shell;

said first shell and said second shell comprising a guiding device for guiding their mutual movement for bringing them closer or moving them away from each other, made possible by the flexibility of said flexible element;

and said first shell has a second peripheral wall forming an internal face, the internal face, when said first shell and the second shell are in their assembling condition, coming into close proximity to said external peripheral face and being able to slide along the latter;

said second peripheral wall of the second shell includes an undercut shape with an opening for introducing the flexible element with a smaller section than the section which this cavity has underneath the opening, said flexible element being deformable so as to be able to forcibly cross the edge of said first peripheral wall delimiting the opening;

said flexible element comprises a third peripheral wall intended to be placed along the internal face of said second peripheral wall of the second shell, a first end face connected to this third peripheral wall, the internal housing on a second end face, opposite to said first end face; said internal housing comprises an undercut shape having an opening with a smaller section than the section which the internal housing has underneath this opening; and said first shell has a stud suitable for being snugly placed in the internal housing, the stud having, at its free end, a larger section than the one which it has at its base, and said flexible element being deformable so that the stud is adapted to forcibly cross the edge of said third peripheral wall of the flexible element delimiting said opening.

2. The prosthesis according to claim 1, wherein:

said first peripheral wall and the bottom wall delimiting said cavity are connected to each other through a first rounded wall having a first radius of curvature;

a third peripheral wall and said first end face of the flexible element are connected to each other through a second rounded wall having a second radius of curvature, the second radius of curvature being larger than the first radius of curvature so that, when said flexible element is engaged into said cavity, there exists a peripheral space between said second rounded wall of the flexible element and said first rounded wall of said second shell; said first end face of the flexible element has a central recess giving it a concave shape, the recess being such that there exists, when said flexible element is engaged into said cavity, a central space between the first end face and said bottom wall.

3. The prosthesis according to claim 2, wherein the surface of said bottom wall delimiting the bottom of the cavity is planar, and said central recess is such that said first end face of the flexible element comes into contact with the planar surface when said first rounded wall of the flexible element comes into contact with said first rounded wall of the second shell.

4. The prosthesis according to claim 2, wherein the surface of said bottom wall delimiting the bottom of the cavity has a concave recess allowing additional flexural deformation of the flexible element beyond the point when said second rounded wall of the flexible element comes into contact with said first rounded wall of the second shell.

5. The prosthesis according to claim 1, wherein the prosthesis includes a dual articular movement having two plates jointed relatively to said intermediate core, said second shell forming an articular surface cooperating with a conjugate articular surface possessed by the second plate of the prosthesis.

6. The prosthesis according to claim 5, wherein the articular surface formed by said second shell and said conjugate articular surface possessed by the second plate of the prosthesis are portions of a sphere.

7. The prosthesis according to claim 5, wherein:

said conjugate articular surface of the second plate is formed by the bottom of a recess delimited by a protruding circular wall, this protruding circular wall having an internal face tilted towards the inside of this recess;

the lower shell comprises a base with smaller dimensions than those of the recess delimited by said protruding circular wall, the edge of which has a tilt corresponding to that of the internal face of this wall.

8. The prosthesis according to claim 1, wherein the prosthesis includes a single articular movement when only one of the two plates is jointed relative to the intermediate core, the second shell being formed by the second plate itself.

9. The prosthesis according to claim 1, wherein the articular surface formed by said first shell and said conjugate articular surface possessed by said first plate are portions of a sphere.

10. An intervertebral disc prosthesis comprising:

a first plate having a central recess limited by a protruding circular wall and a bottom wall, the circular wall having an internal face tilted towards inside of the recess;

a second plate having a central boss on an inner face and insertion studs on an outer face;

an intermediate damping core placed between the first plate and the second plate, the intermediate core comprising;

a first shell forming a first articular surface for cooperating with a conjugate articular surface possessed by the first plate, the first shell including a base, a first peripheral wall delimiting a central cavity, the central cavity has an undercut shape, the first peripheral wall including an internal face that is tilted towards the inside of the central cavity, the tilted internal face of the circular wall of the first plate retains the base of the first shell in a working position;

a second shell forming a second articular surface for cooperating with a conjugate articular surface possessed by the second plate, the second shell including a second peripheral wall having a circular shape and a central stud;

a flexible element placed between the first shell and the second shell; the flexible element having a shape of a cup with a peripheral wall and bottom wall delimiting an internal housing, the internal housing receives the central stud in the working position, the flexible element is tightly secured inside the central cavity of the first shell in the working position, the flexible element is deformable so to be able to forcibly cross the edge of said first peripheral wall delimiting the central cavity, the internal housing of the flexible element secures the central stud of the second shell on the working position;

wherein when the flexible member engages into the central cavity of the first shell, a peripheral space is created between the bottom wall of the flexible element and the base of the first shell;

wherein tilted internal face of the central recess of the first plate tightly secures the intermediate core in the working position;

wherein in the working position, the flexible element by the pressure applied to the first plate and the second plate, deforms inside the central cavity of the first shell joining the first shell and the second shell together and filling the peripheral space between the bottom wall of the flexible element and the base of the first shell.

* * * * *